United States Patent [19]

Carra et al.

[11] Patent Number: 4,766,262

[45] Date of Patent: Aug. 23, 1988

[54] PROCESS FOR SEPARATING ISOMERIC DICHLOROTOLUENES BY ADSORPTION

[75] Inventors: Sergio Carra, Milan; Renato Paludetto, Pioltello; Giuseppe Storti, Lodi; Massimo Morbidelli, Milan, all of Italy; Bernard Gurtner, Grenoble; Raymond Commandeur, Vizille, both of France

[73] Assignee: Atochem, France

[21] Appl. No.: 926,461

[22] Filed: Nov. 3, 1986

[30] Foreign Application Priority Data

Nov. 6, 1985 [FR] France ............................. 85 16446

[51] Int. Cl.$^4$ ..................... C07C 17/38; C07C 25/02
[52] U.S. Cl. .................................................... 570/211
[58] Field of Search ......................................... 570/211

[56] References Cited

U.S. PATENT DOCUMENTS

| | | | |
|---|---|---|---|
| 2,958,708 | 11/1960 | Fleck et al. ........................ | 570/211 |
| 3,615,188 | 10/1971 | Kouwenhoven et al. ........... | 502/78 |
| 3,758,667 | 9/1973 | Kouwenhoven et al. ........... | 502/78 |
| 4,254,062 | 3/1981 | Wambach et al. ................. | 570/211 |
| 4,453,029 | 6/1984 | Dessau ............................. | 585/820 |

FOREIGN PATENT DOCUMENTS 2166734  5/1986  United Kingdom ............... 570/211

Primary Examiner—J. E. Evans
Attorney, Agent, or Firm—Sigalos, Levine & Montgomery

[57] ABSTRACT

A process for separating dichlorotoluene isomers from a mixture containing at least two dichlorotoluene isomers comprising
(a) passing said mixture containing dichlorotoluene isomers through a mordenite having the following composition; in molar ratios:
a $H_2O$: b $M_{2/n}O$: $Al_2O_3$: (10–400 $SiO_2$)
in which M is hydrogen or at least one cation selected from an alkali metal or an alkaline-earth metal with the exception of cesium and rubidium, n is the valence of M, $0.7 \leq a+b \leq 1.1$, and $0 \leq b \leq 0.2$,
(b) separating the non-adsorbed dichlorotoluenes from said mordenite,
(c) contacting said mordenite containing the adsorbed isomers with a desorbent capable of separating said isomers from said mordenite, and
(d) separating the desorbed isomers from the desorbent.

9 Claims, No Drawings

PROCESS FOR SEPARATING ISOMERIC DICHLOROTOLUENES BY ADSORPTION

BACKGROUND OF THE INVENTION

The present invention pertains to a process for separating isometric dichlorotoluenes by adsorption on certain zeolites.

Dichlorotoluenes are generally prepared by chlorinating toluene or monochlorotoluenes in the presence of a Lewis acid such as the trichlorides of aluminum, iron or antimony alone or combined with a cocatalyst, e.g., sulfur or sulfur chlorides.

The chlorination reaction leads to the formation of mixtures containing dichloro -2,4, -2,5, -2,6, -3,4 and -2,3 toluenes. These mixtures can be separated by distillation of the other chlorinated products of toluene or monochlorotoluenes (monochlorotoluene and trichlorotoluenes). The five above-mentioned isomers are obtained in varying proportions depending on the starting products used in the chlorination reaction.

The dichlorotoluene mixtures can also be separated by distillation into two fractions boiling at ca. 201° C. and ca. 209° C. The first fraction comprises the -2,6, -2,4 and -2,5 isomers, and the second fraction consists of the -3,4 and -2,3 isomers.

It has also been generally admitted that it is not possible to obtain all the different isomers in the pure state under economically acceptable conditions according to the conventional distillation or fractionated crystallization techniques. The distillation does not permit, in particular, separating the constituents of the two fractions boiling at ca. 201° C. and ca. 209° C. due to the very small difference between the boiling points of the isomers. Only the dichloro-2,3-toluene can be separated by distillation, provided that o-chlorotoluene is used as the starting product. As far as fractionated crystallization is concerned, it is not generally suitable due to the existence of numerous eutectic mixtures.

In view of the above considerations, other separation techniques have been proposed. In particular, U.S. Pat. No. 4,254,062 discloses a process for separating the isomeric dichlorotoluenes by means of type X or Y zeolites.

SUMMARY OF THE INVENTION

The present invention proposes a new process for separating the dichlorotoluene isomers.

Briefly, the present invention comprises a process for separating dichlorotoluene isomers from a mixture containing at least two dichlorotoluene isomers comprising (a) passing said mixture containing dichlorotoluene isomers through a mordenite having the following composition; in molar ratios:

a $H_2O$:b $M_{2/n}O$:$Al_2O_3$:(10–400 $SiO_2$)

in which M is at least one cation selected from an alkali metal or an alkaline-earth metal with the exception of cesium and rubidium, n is the valence of M, $0.7 \leq a+b \leq 1.1$, and $0 \leq b \leq 0.2$, (b) separating the non-absorbed dichlorotoluenes from said mordenite, (c) contacting said mordenite containing the adsorbed isomers with a desorbent capable of separating said isomers from said mordenite, and (d) separating the desorbed isomers from the desorbent.

In the above formula, M is preferably sodium.

DETAILED DESCRIPTION

Mordenites are naturally occurring zeolite mineral and those preferably used in the process according to the present invention are characterized by a tubular structure, orthorhombic symmetry, and they possess the lattice parameters (X-ray diffraction): a=18.1 Å, b=20.2 to 20.4 Å and c=7.4 to 7.5 Å with the canals being paralle to the c axis.

The process according to the present invention can be used in liquid phase or in vapor phase. This adsorption-desorption process can be carried out between about 25° C. and 350° C. and in a broad pressure range (e.g., under pressures ranging from ca. 1 bar to ca. 30 bar).

The dichlorotoluene isomers can be contacted with the mordenite in a conventional adsorption-separation device. It is especially possible to use devices permitting continuous or batch operations. The form and the dimensions of the said devices can be optimized by the person skilled in the art and they are not themselves within the scope of the present invention.

In general, the mordenite used in the adsorption-desorption device, e.g., in an adsorption column, is in the form of particles whose mean dimensions are between 0.1 and 10 mm, and preferably between 0.5 and 5 mm.

The said mordenite is brought into contact with the dichlorotoluene isomer mixture. Even though the adsorption capacity of this type of zeolite with respect to the said five isomers in itself permits the separation of the five isomers, it is possible to only send a mixture containing only a part of the said isomers to the mordenite. Thus, after separation of the -2,3 and -3,4 isomers (which boil at ca. 209° C.) by distillation, it is possible to subject only the aforementioned fractions to the adsorption-desorption, as the mordenite adsorbs the -3,4 and -2,3 isomers differently, on the one hand, and the -2,4 -2,5 and -2,6 isomers, on the other hand. It is, of course possible to treat mixtures preliminarily concentrated with respect to at least one of the said isomers by the process according to the present invention.

As was stated above, the isomer mixture, total or partial, is partially adsorbed on the mordenite. The non-adsorbed dichlorotoluenes can be collected at the outlet of the adsorption-desorption device. The mordenite is then brought into contact with an eluent or desorbent; that is, a compound permitting the isomers to be displaced and then to be separated. A compound whose action on the mordenite is on the same order of magnitude as that of the dichlorotoluenes in question is preferably selected. Examples of desorbents suitable for use in the instant process are hydrogen, nitrogen, oxygen, carbon dioxide, helium, hydrocarbons and especially alkanes such as methane, ethane, propane, n-hexane, n-heptane, n-octane, iso-octane, cycloalkanes and especially cyclohexane, monocyclic or polycyclic aromatic compounds, which may be unsubstituted or substituted (preferably halogenated), such as benzene, toluene, ethyl benzene, cumene, tetrahydronaphthalene, decahydronaphthalene, as well as mono- and dichlorotoluenes.

Iso-octane, benzene, monochlorobenzene or dichlorobenzenes are preferably used according to the present invention.

After the action of the desorbent or eluent agents, the isomers proper can be separated from the said agents by conventional methods; e.g., distillation.

In general, the process according to the present invention permits the composition of mixtures containing five dichlorotoluene isomers to be modified due to the remarkable selectivity of mordenite. This selectivity is defined by the fraction:

$$S_{i/j} = \frac{\dfrac{\text{molar fraction of isomer } i \text{ in the desorbate}}{\text{molar fraction of isomer } j \text{ in the desorbate}}}{\dfrac{\text{molar fraction of } i \text{ in the initial mixture}}{\text{molar fraction of } j \text{ in the initial mixture}}}$$

In particular, this process permits the fractions boiling at 201° C. and 209° C. to be separated into their constituents and, from the fraction boiling at 201° C., which consists of the -2,4, -2,5 and -2,6 isomers, it permits the -2,6 isomer to be obtained in a highly efficient manner.

The present invention will be illustrated by the following examples which are set forth for purposes of illustration only. A modernite of the molar composition of 0.1 $Na_2O$:0.9 $H_2O$:$Al_2O_3$:18 $SiO_2$ was used as the zeolite in these examples; this mordenite is in the form of particles with a diameter of 3 mm.

This mordenite is commercially available from Societe Chimique de la Grande Paroisse under the trademark ALITE 180.

The dichlorotoluene isomer mixture used is formed either by the industrial product obtained by chlorinating toluene (Example 1) or by the fractions of the said industrial product which boils at ca. 209° C. and ca. 201° C., or finally, by compositions in which the proportions of the constituents were varied; the experiments were carried out in the vapor phase (adsorption temperature: 220° C.) or in the liquid phase (25° C.).

The experiments were carried out in a column with a diameter of 1 cm and a height of 1 m, containing 10 g of mordenite. Nitrogen at a temperature of 450° C. was passed through the mordenite for 16 hours before the experiments, after which the mordenite was saturated with the monochlorobenzene. 10 $cm^3$ of the dichlorotoluene isomer mixture were introduced into the column at a flow rate of 0.5 $cm^3$/minute.

Then, 15 $cm^3$ monochlorobenzene were passed through the column at the same flow rate of 0.5 $cm^3$/minute. The solution of the dichlorotoluene isomers in the monochlorobenzene was collected, and the molar composition of the desorbate was determined.

EXAMPLE 1

(Vapor Phase)

The instant process was applied to an industrial mixture of dichlorotoluene isomers utilizing the mordenite, isomer mixture, and apparatus, and process conditions described above. The results are set forth in Table I and the abbreviations used in the table have the following meanings:

dct isomer: dichlorotoluene isomer
mol.% at inlet: molar fraction of the isomer in question in the composition subjected to the adsorption/desorption
mol.% at outlet: molar fraction of the isomer in question in the desorbate
selectivity/-2,6: selectivity of the isomer in question with respect to the -2,6 isomer.

The selectivity is stated with reference to the -2,6 isomer so as not to crowd the table, but it is certain that it can easily be calculated for any two pair of isomers from the formula above.

TABLE I

| dct isomer | Mol. % at inlet | Mol. % at outlet | Selectivity/−2,6 |
|---|---|---|---|
| −2,5 | 36.95 | 38.92 | 1.43 |
| −2,6 | 8.34 | 6.13 | 1.0 |
| −2,4 | 33.55 | 34.73 | 1.41 |
| −3,4 | 12.92 | 14.23 | 1.50 |
| −2,3 | 7.62 | 6.00 | 1.07 |

EXAMPLE 2

(Vapor Phase)

The above-described procedure is applied to the fraction of the industrial product boiling at 201° C. The results are set forth in Table II.

TABLE II

| | Initial composition (mol. %) | | | Desorbate composition (mol. %) | | | Selectivity −2,4/−2,6 −2,4/−2,5 |
|---|---|---|---|---|---|---|---|
| Example | −2,5 | −2,6 | −2,4 | −2,5 | −2,6 | −2,4 | −2,5/−2,6 |
| 2 | 33.40 | 33.19 | 33.23 | 39.11 | 23.62 | 37.27 | 1.58 1.64 1.04 |

EXAMPLES 3 THROUGH 5

(Vapor Phase)

The above-described process is applied to compositions containing two of the three isomers of the fraction boiling at 201° C. and the results set forth in Table III.

TABLE III

| Example | Initial composition (mol. %) | | | Desorbate composition (mol. %) | | | Selectivity (S) |
|---|---|---|---|---|---|---|---|
| | −2,5 | −2,6 | −2,4 | −2,5 | −2,6 | −2,4 | |
| 3 | 49.95 | 50.05 | — | 63.78 | 36.22 | — | S−2,5/−2,6 = 1.76 |
| 4 | — | 50.00 | 50.00 | — | 36.49 | 63.51 | S−2,4/−2,6 = 1.74 |
| 5 | 50.35 | — | 49.65 | 51.05 | — | 48.95 | S−2,5/−2,4 = 1.03 |

EXAMPLES 6 THROUGH 8

(Vapor Phase)

The process is applied to mixtures of the -2,4 and -2,6 isomers at varying ratios and the results set forth in Table IV.

TABLE IV

| | Initial composition (mol. %) | | Desorbate composition (mol. %) | | Selectivity |
|---|---|---|---|---|---|
| Example | −2,4 | −2,6 | −2,4 | −2,6 | −2,4/−2,6 |
| 6 | 10.70 | 89.30 | 21.70 | 78.30 | 2.31 |
| 7 | 17.13 | 82.87 | 27.12 | 72.88 | 1.80 |
| 8 | 39.72 | 60.28 | 55.72 | 44.28 | 1.91 |

EXAMPLES 9 AND 10

(Vapor Phase)

The process is applied to mixtures of the -2,5 and -2,6 isomers at varying rations and results set forth in Table V.

TABLE V

| | Initial composition (mol. %) | | Desorbate composition (mol. %) | | Selectivity |
|---|---|---|---|---|---|
| Example | −2,5 | −2,6 | −2,5 | −2,6 | −2,5/−2,6 |
| 9 | 25.03 | 74.97 | 42.42 | 57.58 | 2.21 |

TABLE V-continued

| Example | Initial composition (mol. %) | | Desorbate composition (mol. %) | | Selectivity |
| --- | --- | --- | --- | --- | --- |
| | −2,5 | −2,6 | −2,5 | −2,6 | −2,5/−2,6 |
| 10 | 59.72 | 40.28 | 72.75 | 27.25 | 1.80 |

EXAMPLES 11 AND 12

(Liquid Phase)

The separation test with the -2,4, -2,5 and -2,6 isomer mixtures is repeated in the liquid phase with solutions in iso-octane at 25° C. and results set forth in Table VI.

TABLE VI

| Example | Isomers | % of isomer in the | | Relative % of the two isomers | |
| --- | --- | --- | --- | --- | --- |
| | | initial | final | initial | final |
| | | solution | | | |
| 11 | −2,4 | 5.73 | 5.05 | 50 | 46.30 |
| | and −2,6 | 5.74 | 6.00 | 50 | 53.70 |
| 12 | −2,5 | 5.76 | 5.16 | 50 | 46.30 |
| | and −2,6 | 5.77 | 5.99 | 50 | 53.70 |

It is apparent from this table that the absolute percentage of the -2,6 isomer in the final solution is practically identical with the initial percentage, whereas the decreases in the concentrations of the -2,4 and -2,5 isomers are evident. Consequently, high selectivity is observed in the liquid phase as well.

EXAMPLES 13 AND 14

The liquid-phase experiment from Example 11 was repeated with ternary mixture (Example 13) or with the commercial product (Example 14). The following results were obtained:

TABLE VIII

| Example | Isomers | % of isomer in the | | Relative % of the two isomers | |
| --- | --- | --- | --- | --- | --- |
| | | initial | final | initial | final |
| | | solution | | | |
| 13 | −2,5 | 3.81 | 3.32 | 33.48 | 31.41 |
| | −2,6 | 3.79 | 3.90 | 33.30 | 36.90 |
| | −2,4 | 3.78 | 3.35 | 33.22 | 31.65 |
| 14 | −2,5 | 4.24 | 3.87 | 37.19 | 36.44 |
| | −2,6 | 0.96 | 0.98 | 8.42 | 9.23 |
| | −2,4 | 3.85 | 3.54 | 33.77 | 33.33 |
| | −3,4 | 1.48 | 1.31 | 12.98 | 12.34 |
| | −2,3 | 0.87 | 0.92 | 8.07 | 8.66 |

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. A process for separating one or more dichlorotoluene isomers from one or more different dichlorotoluene isomers in a mixture containing at least two dichlorotoluene isomers comprising
   (a) passing said mixture containing dichlorotoluene isomers through a mordenite having the following composition; in molar ratios:

a $H_2O$:b $M_{2/n}O$:$Al_2O_3$:(10–400 $SiO_2$)

in which M is at least one cation selected from an alkali metal or an alkaline-earth metal with the exception of cesium and rubidium, n is the valence of M, $0.7 \leq a+b \leq 1.1$, and $0 \leq b \leq 0.2$,
   (b) separating the non-adsorbed dichlorotoluenes from said mordenite,
   (c) contacting said mordenite containing the adsorbed isomers with a desorbent capable of separating said isomers from said mordenite, and
   (d) separating the desorbed isomers from the desorbent.

2. The process of claim 1, wherein M is a sodium cation.

3. The process of claim 1, wherein the mordenite has a tubular structure, orthorhombic symmetry and the following lattice parameters (X-ray diffraction): a=18.1 Å, b=20.2 to 20.4 Å and c=7.4 to 7.5 Å with the canals being parallel to the c axis.

4. The process of claim 1, 2, or 3, wherein contacting of the dichlorotoluene isomer mixture with the mordenite is carried out in the liquid or gaseous phase at a temperature between about 25° C. to 350° and under a pressure between about 1 bar to 30 bar.

5. The process of claim 1, 2, or 3, wherein the mixture brought into contact with the mordenite comprises the -2,3, -3,4, -2,4, -2,5 and -2,6 dichlorotoluene isomers.

6. The process of claim 1, wherein the mixture brought into contact with the mordenite is formed by dichloro-2,3 and -3,4 toluenes.

7. The process of claim 1, wherein the mixture brought into contact with the mordenite is formed by the dichloro-2,4, -2,5 and -2,6 toluenes.

8. The process of claim 6 or 7, wherein the mixture brought into contact with the mordenite is preliminarily concentrated in at least one of its constituents.

9. The process of claim 1, wherein the desorbent is selected from hydrogen, nitrogen, alkanes, or monocyclic or polycyclic substituted or unsubstituted aromatic hydrocarbons.

* * * * *